(12) United States Patent
Burke et al.

(10) Patent No.: US 8,043,270 B2
(45) Date of Patent: Oct. 25, 2011

(54) PHARMACEUTICAL ANALYSIS APPARATUS AND METHOD

(75) Inventors: Matthew D Burke, Research Triangle Park, NC (US); Chinmay R Maheshwari, Research Triangle Park, NC (US); Brian O Zimmerman, Research Triangle Park, NC (US)

(73) Assignee: GlaxoSmith Kline LLC, Philadelphia, PA (US)

( * ) Notice: Subject to any disclaimer, the term of this patent is extended or adjusted under 35 U.S.C. 154(b) by 1097 days.

(21) Appl. No.: 11/718,541

(22) PCT Filed: Nov. 3, 2005

(86) PCT No.: PCT/US2005/039991
§ 371 (c)(1),
(2), (4) Date: May 3, 2007

(87) PCT Pub. No.: WO2006/052742
PCT Pub. Date: May 18, 2006

(65) Prior Publication Data
US 2008/0020468 A1 Jan. 24, 2008

Related U.S. Application Data

(60) Provisional application No. 60/625,620, filed on Nov. 5, 2004.

(51) Int. Cl.
*A61M 37/00* (2006.01)
(52) U.S. Cl. .................................. 604/288.01
(58) Field of Classification Search ............... 604/890.1, 604/891.1, 892.1, 131, 140, 141, 19, 96.01, 604/101.01, 93.01, 288.01, 288.04
See application file for complete search history.

(56) References Cited

U.S. PATENT DOCUMENTS

| | | | | |
|---|---|---|---|---|
| 4,576,604 A | * | 3/1986 | Guittard et al. | 424/473 |
| 5,062,841 A | * | 11/1991 | Siegel | 604/891.1 |
| 5,395,366 A | * | 3/1995 | D'Andrea et al. | 604/890.1 |
| 5,443,459 A | | 8/1995 | Wong et al. | |
| 7,063,691 B2 | * | 6/2006 | Nelson et al. | 604/891.1 |

* cited by examiner

*Primary Examiner* — Manuel Mendez
(74) *Attorney, Agent, or Firm* — Dwight S. Walker (57) ABSTRACT

An apparatus and method are provided for analyzing the release of active agent(s) from pharmaceutical and pharmaceutical-like products. The apparatus and method provide for more accurate simulation of the conditions in the GI tract including forces that are applied to the dosage form.

12 Claims, 7 Drawing Sheets

Fig. 9

PHARMACEUTICAL ANALYSIS APPARATUS AND METHOD

This application is a §371 application of PCT/US2005/039991 filed 3 Nov. 2005, which claims the benefit of U.S. Provisional Application No. 60/6,256,620, filed 5 Nov. 2004.

BACKGROUND OF THE INVENTION

1. Field of the Invention

The present invention relates to the analysis of pharmaceutical and pharmaceutical-like products. More particularly, the present invention relates to an apparatus and process for analyzing and/or predicting the release of active agents in pharmaceutical and pharmaceutical-like products.

2. Description of Related Art

Contemporary dissolution devices include a basket-type, a paddle-type and a reciprocating cylinder-type. For example, the contemporary paddle type dissolution apparatus has a glass, round-bottomed vessel with an impeller mixing the contents of the vessel. The apparatus can also have an auto-sampler shaft inserted into the vessel to collect samples at selected intervals of time from an aqueous solution in the vessel. A tablet to be analyzed is dropped into the vessel and falls to the bottom of the vessel, where it sits during the dissolution run. The basket and reciprocating cylinder-type dissolution devices similarly provide for mixing of the solution in the device while the tablet rests in the vessel.

These contemporary dissolution devices were designed for quality control of drug release rates. The contemporary dissolution devices suffer from the drawback of failing to adequately replicate the conditions that a dosage form encounters in the gastro-intestinal (GI) tract, e.g., the stomach and/or intestine. None of these contemporary devices simulate or account for the forces applied to the dosage form due to the digestive conditions and peristaltic actions along the GI tract.

Figure 1:
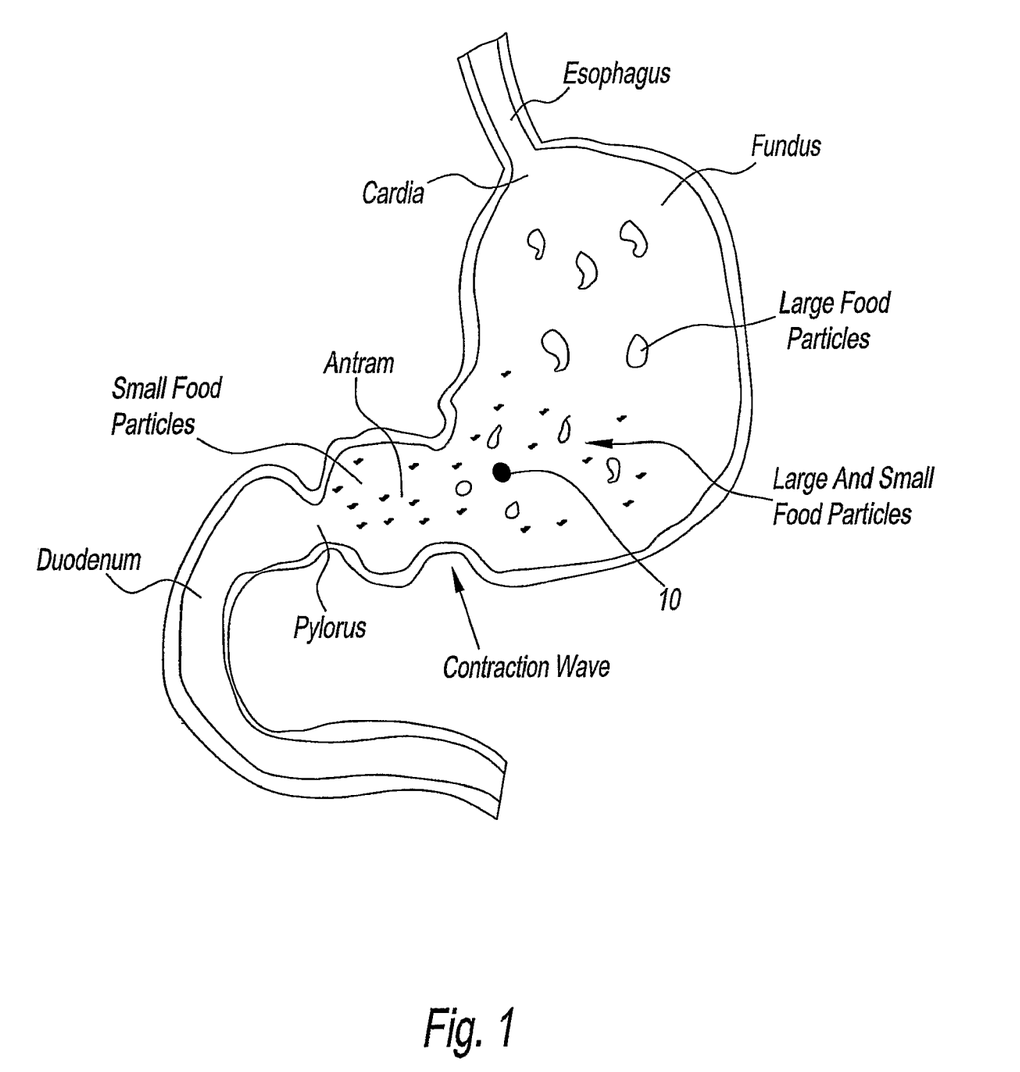
FIG. 1 is a schematic representation view of a portion of a human upper GI tract.
Figure 2:
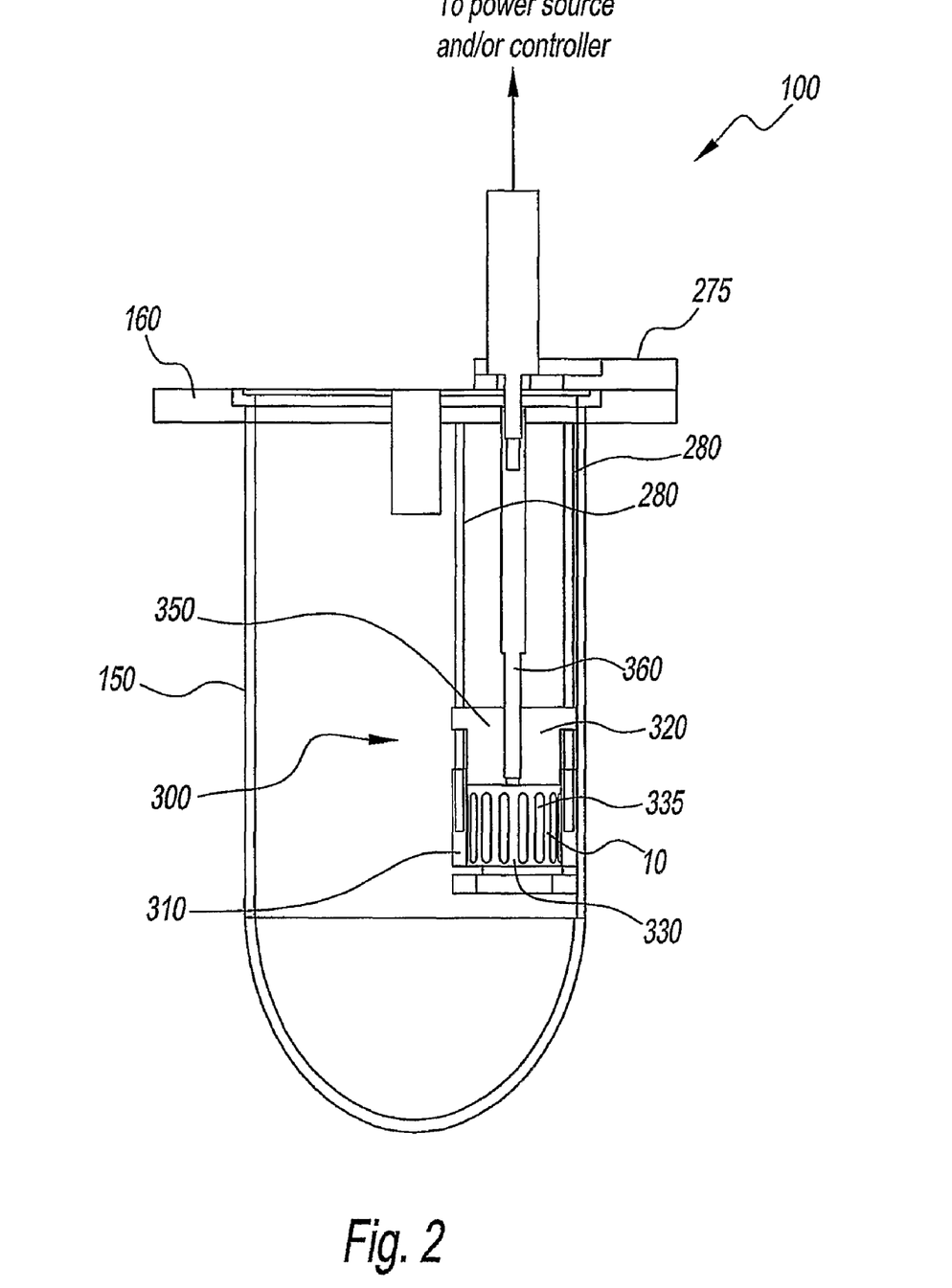
FIG. 2 is a plan view of an analyzing device of the present invention without an impeller and a sampler.

As shown in FIG. 1, food and liquids are present in the GI tract, in addition to digestive muscular contractions, mass movement, compression, peristalsis, and other forces. All of these conditions can play a key role in the rate of drug release, especially for controlled or extended release products. These mechanically destructive forces are clearly present and are imparted on a dosage form as it travels along the GI tract.

Accordingly, there is a need for an apparatus and process for analyzing and predicting the release of active pharmaceutical ingredients (API) or active agents from pharmaceutical and pharmaceutical-like products. There is a further need for such an apparatus and process that more adequately replicates or simulates the conditions in the GI tract.

SUMMARY OF THE INVENTION

It is an object of the present invention to provide a more accurate process and apparatus for analyzing and/or predicting release of active agents from pharmaceutical and pharmaceutical-like products.

It is another object of the present invention to provide such a process and apparatus that more adequately replicates or simulates the conditions found in the GI tract.

It is yet another object of the present invention to provide such a process and apparatus that more efficiently performs such analysis and/or prediction of the active agent(s) release.

These and other objects and advantages of the present invention are provided by an apparatus for analyzing the release of an active agent(s) from a pharmaceutical product or pharmaceutical-like produce, which more accurately simulates the conditions in the GI tract by applying forces to the dosage form. The frequency, duration and amount of force or compression that is applied to the dosage form can be controlled and preferably varied. This is preferably done by a programmable logic computer (PLC). The analysis device is preferably retro-fittable to existing dissolution devices to render such contemporary devices more accurate in simulating the conditions in the GI tract.

Other and further objects, advantages and features of the present invention will be understood by reference to the following:

DETAILED DESCRIPTION OF THE INVENTION

Referring to the drawings, and in particular FIG. 1, a pharmaceutical product or dosage form 10 traveling along the human GI tract is subjected to forces from a variety of sources including food and liquids that are present therein, digestive muscular contractions, mass movement, compression, peristalsis, and other forces. These forces act upon the dosage form 10, effecting the release of the dosage form's active agent(s). It should be understood that while the following disclosure describes the pharmaceutical product or pharmaceutical-like product as a dosage form 10, the present invention contemplates analysis of any type of pharmaceutical product or pharmaceutical-like product that has an active agent(s) which is released, such as, for example, tablets, capsules, caplets, or other dosage forms.

Referring to FIGS. 2 through 5, a preferred embodiment of the pharmaceutical analysis apparatus or device of the present invention is shown and generally referred to by reference numeral 100. The device 100 has a housing 150, a top 160, an impeller 200, a sampler 250, a connecting or mounting plate 275, and a force application system 300.

The housing 150 holds the solution, e.g., an aqueous solution, which simulates the medium in the human GI tract. The housing 150 is a transparent, round-bottomed vessel. However, the present invention contemplates the use of other materials and other shapes for the housing 150, which facilitate use of the analysis device 100 and/or more accurate simulation of the conditions of the GI tract.

Figure 5:
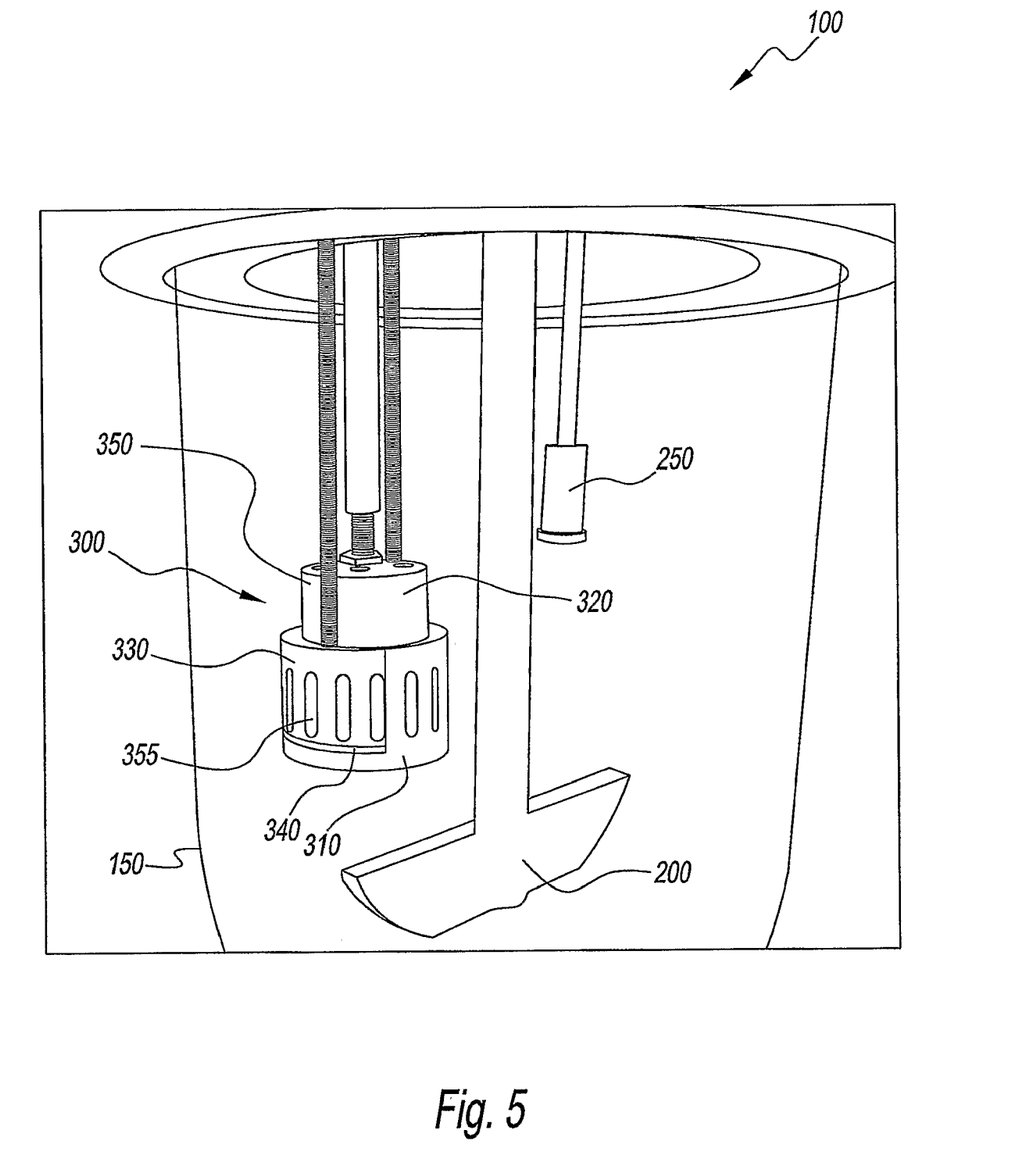
FIG. 5 is a perspective view of the device of FIG. 2 with the impeller and the sampler.

The impeller 200 provides motion to the aqueous solution to distribute the active agent in the solution and to further simulate the conditions of the GI tract. The present invention contemplates the use of various shapes and sizes for the impeller 200, as well as various directions of movement for the impeller (e.g., rotational and/or axial), which can facilitate distribution of the active agent in the solution and/or more accurately simulate the conditions in the GI tract. The present invention also contemplates the use of other devices for distributing the active agent in the solution and for simulating the motion of the medium, solution and/or dosage form 10 in the GI tract, such as, for example, a reciprocating cylinder in a cylindrical vessel.

The sampler 250 obtains samples of the aqueous solution to determine the amount of active agent that has been released by the dosage form 10. Preferably, the sampler 250 is operably connected to a controller, such as, for example, a control processing unit or PLC (not shown), which can selectively obtain the sample, process it, and/or analyze it. Such analysis of the sample of the solution includes, but is not limited to, UV analysis. However, the present invention contemplates the use of various techniques of analysis of the sample of solution.

The force application system 300 is mounted or connected with the housing 150 of the analysis device 100, and in particular with the top 160, through use of connecting plate 275. Connecting plate 275 allows for retrofitting of the force application system 300 with a contemporary dissolution device. However, the present invention contemplates the use of other structures and methods of mounting or connecting the force application system 300 to the housing 150 or to a contemporary dissolution device. The connecting plate 275 has a number of supports 280 that allow the force application system 300 to be positioned below the connecting plate into the solution.

The present invention also contemplates the supports 280 being adjustable so that the position of the force application system 300 in the solution can be selectively varied. The present invention further contemplates the use of other structures and methods for positioning the force application system 300 in a selected position in the housing 150.

Figure 3:
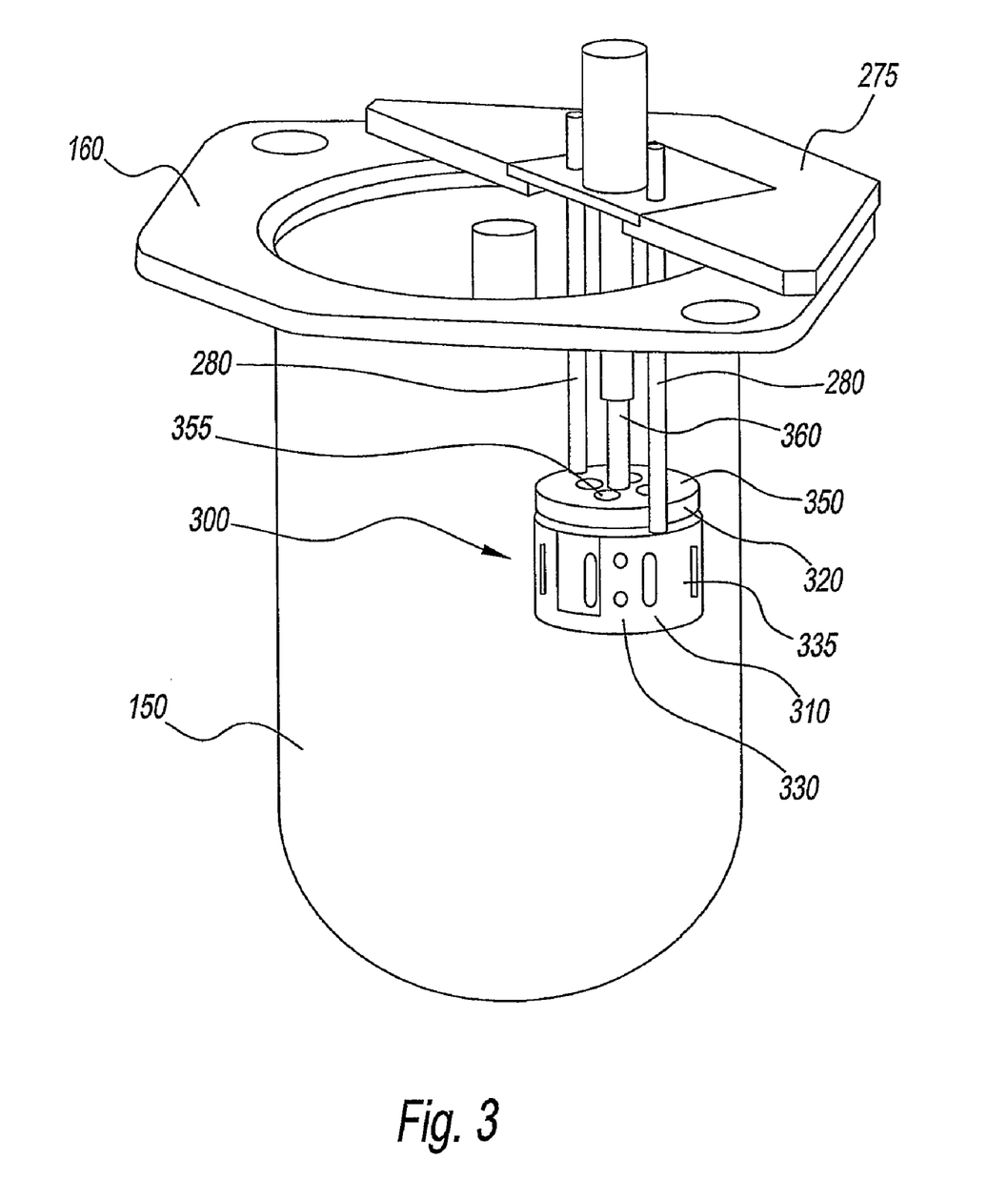
FIG. 3 is a perspective view of the device of FIG. 2 with the force application system actuated.
Figure 4:
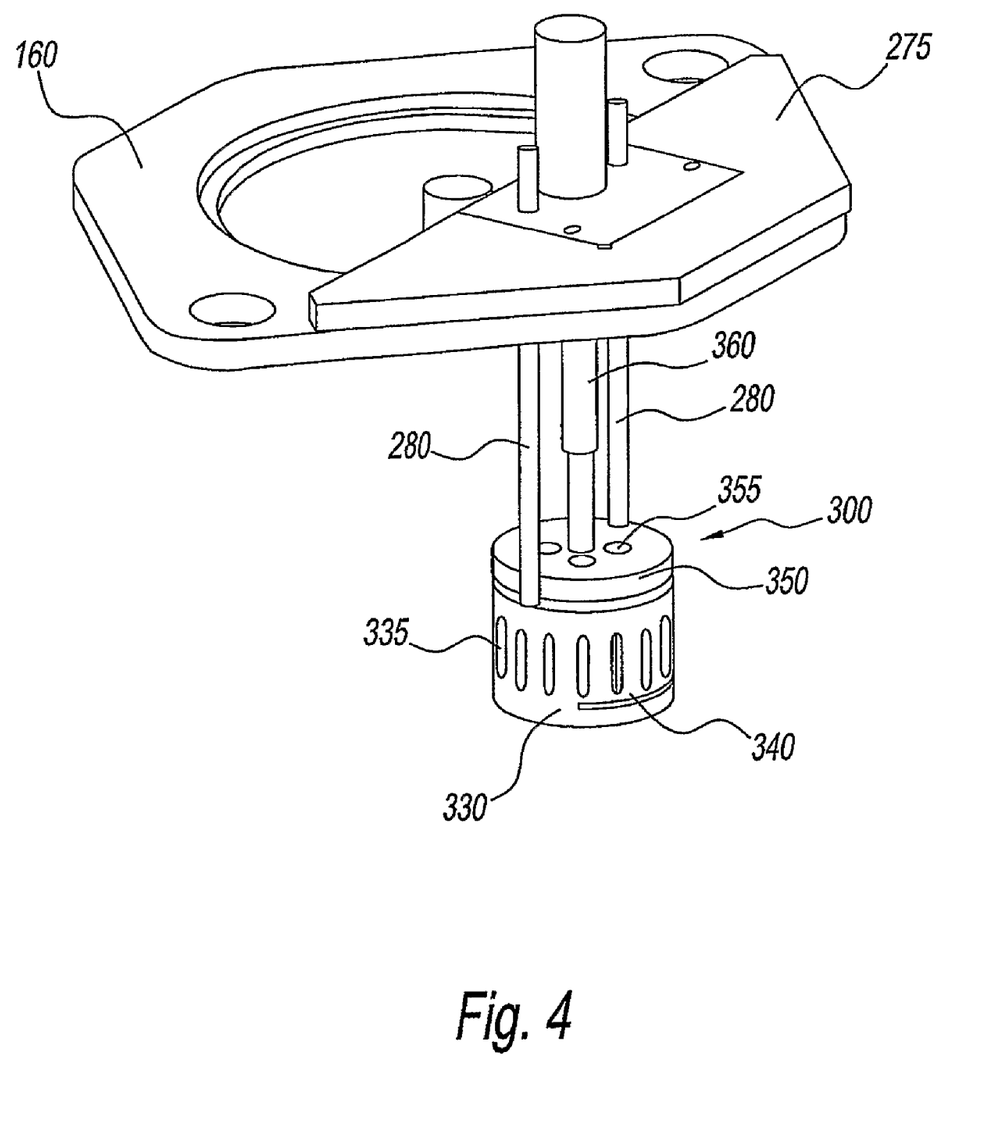
FIG. 4 is a perspective view of a portion of the device of FIG. 3.

The force application system 300 has a dosage form housing 310 and a force imparting mechanism 320. In the embodiment shown, the dosage form housing 310 is a cylindrical chamber 330 having a mesh screen 340 along the bottom of the chamber. The cylindrical chamber 330 has a number of side slots 335, which allow for flow of the aqueous solution into and through the chamber. The mesh screen 340 is a floor for the chamber 330 upon which the dosage form 10 sits. Where a specific orientation of the dosage form 10 is desired, such as, for example, when analyzing a bi-layer tablet, two mesh screens 340 can be used to sandwich the dosage form in place.

In the embodiment shown, the force imparting mechanism 320 is a piston 350. The piston 350 has a number of holes 355 formed therethrough, which allow for flow of the aqueous solution into the chamber 330. The piston 350 is connected to a drive shaft 360, which can be actuated by a power source (not shown), which in this embodiment is a pneumatic cylinder. However, the present invention contemplates the use of other power sources, such as, for example, a mechanical cam or electrical solenoid.

In an alternative embodiment (not shown), the force application system 300 has a contact medium. The contact medium would be positioned or located on the force application system 300, where the force is imparted to the dosage form 10. For example, where force application system 300 utilizes piston 350, the contact medium could be on the piston and would make contact with the dosage form 10. The contact medium may be a silicon padding on the lower portion of piston 350 (e.g., on the ceiling of the force application system 300). The contact medium can also be a wire mesh on the lower portion of piston 350 (e.g., on the ceiling of the force application system 300).

Where the contact medium is a wire mesh, it may be assembled with various degrees of tensions (such as, for example, very tight or very loose), depending on the requirement for the dissolution method. A loose wire mesh would be used to apply the force gently on the dosage form 10, to simulate a peristaltic contraction. Wire meshes of various thicknesses of wires and various numbers of openings per square inch can be used for the contact medium.

The present invention contemplates the substantially solid piston 350 of the embodiment of FIGS. 2 through 5 being modified by attaching or connecting the contact medium, such as, for example, a perforated FDA approved silicon padding. The silicon padding can be of various thicknesses depending on the dissolution method. The use of the silicon pad mimics or simulates the environment of the GI soft tissue wall and mimics or simulates the GI peristaltic contractions.

The present invention contemplates the use of other materials and/or combinations of materials for the contact medium, which will simulate the conditions that the dosage form 10 is exposed to when in the GI tract. While this alternative embodiment has the contact medium positioned along the bottom portion of piston 350, the present invention contemplates the contact medium being located in various positions along the force application system 300, which will simulate the conditions that the dosage form 10 is exposed to when in the GI tract.

Referring back to the embodiment shown in FIGS. 2 through 5, the power source is preferably operably connected to a programmable timer or the PLC so as to automate the device 100, facilitate control of the analysis process, and allow for accurate reproduction of the analysis of dosage form 10. Force application system 300 is preferably made from electropolished stainless steel. While the dosage form housing 310 and the force imparting mechanism 320 are described in the preferred embodiment as a piston-cylinder assembly, the present invention contemplates other assemblies and devices that allow force imparting mechanism 300 to selectively apply force to the dosage form 10. Such alternative assemblies or devices preferably allow for control of the amount, duration and frequency of the compression. Additionally, such alternative assemblies also contemplate application of multiple forces and/or at varying angles to the dosage form 10 to simulate the conditions in the GI tract.

The programmable timer or PLC is used to set the time that the piston 350 stays in the down position (i.e., the compression state), the frequency at which compression occurs, and the amount of compression. The use of the PLC in conjunction with the adjustability provided by the force application system 300, allows the analysis device 100 to vary the forces (duration, frequency, amount) that are applied to the dosage form 10. The present invention also contemplates use of this controlled variation of force over the duration of the analysis to more accurately simulate the conditions that the dosage form is subjected to as it travels along the GI tract.

Cylindrical chamber 330 preferably has an outer diameter of about 32 mm, an inner diameter of about 24 mm, and a height of about 26 mm. The side slots 335 in cylindrical chamber 330 preferably are about 14 mm in height and about 2.6 mm in width. To hold the mesh screen 340 in place in the cylindrical chamber 330, there are two cuts in the lower part of the chamber that are preferably about 22 mm in width and 1.5 mm in height, so that the screen material can be inserted therein.

The cylindrical chamber 330 is preferably located about 8 cm below the connecting plate 275. The piston 350 preferably has an outer diameter of about 23.5 mm and a height of about 19 mm. The piston 350 has four holes 355 drilled axially through the piston that preferably each have a diameter of about 6.3 mm to allow for the fluid flow therethrough. While this embodiment uses the above described dimensions to simulate the conditions in a human GI tract, the present invention contemplates the use of other dimensions to facilitate control of the analysis process and allow for accurate reproduction of the analysis of dosage form 10.

The present invention contemplates the use of other materials for the mesh screen 340 such as stainless steel or suitable plastics, such as those used in the traditional USP 3 dissolution apparatus. The mesh size of the mesh screen 340 can also be varied as appropriate for the particular dosage form 10.

The pneumatic cylinder, which provides for the motion of the piston 350, is connected to the programmable timer or PLC via two tubes (not shown) and a compressed air source is connected to the programmable timer with a regulator (not shown) connected to adjust the air pressure. The regulator can be used to control the force that is imparted upon the dosage form 10 via regulating the amount of air pressure. As the piston 350 moves to the lower position, it compresses the dosage form 10 against the mesh screen 340 thus applying a mechanical stress to the dosage form 10 simulating the in-vivo forces that the dosage form would experience.

The device 100 is flexible in its settings and sizes. The materials used for force application system 300 are those that are able to withstand prolonged exposure to acid and to basic pH with and/or without various surfactants commonly used in pharmaceutical dissolution analysis. However, it has been found that certain materials are not properly suited for the process described above. Materials that have been found to be inadequate for these purposes are untreated stainless steel, thinly coated PTFE stainless steel, and hard anodized stainless steel. Such materials corroded after a series of experiments when using acid pH dissolution media. One such material that was found to be usable in the above-described apparatus was electropolished stainless steel.

The overall dimensions of the device 100 are dictated in part by the size of the vessel or housing 150, the size of the impeller 200, the size of the impeller shaft and location, the size of the sampler tube 250, and any filter being used. The maximum diameter of the chamber 330 and piston 350 would preferably be the size that fits into the housing 150 but does not contact the side of the housing, impeller 200 and sampler 250. Preferably, the maximum diameter of the chamber 330 and piston 350 is only as large as the maximum size that the formulation analyzed achieves. However, this maximum size can be fairly large when considering large swelling shapes for gastric retention. When evaluating expanding gastric retentive dosage forms, the mesh screen 340 can be replaced by a component similar in shape to a funnel with a fixed or modulated opening of a size similar to a pyloric sphincter. By recording the time the formulation is retained in the chamber, one can predict when gastric emptying of the dosage form will occur in-vivo.

Where the components of device 100 are retrofitted to a USP 2 paddle-type dissolution apparatus, the device is able to utilize all of the benefits of the traditional USP 2 apparatus, and add an advantage of the ability to hold the dosage form 10 in a piston type device (force application system 300) that is able to apply physical force to the dosage form periodically to simulate the in-vivo forces that the dosage form will be exposed to. The targeted types of dosage forms that will benefit more from this analysis are, for the most part, controlled or extended release products. However, the present invention contemplates the use of this apparatus and method on all types of pharmaceutical products including immediate release dosage forms.

It should be understood that the apparatus and method described herein has been discussed with respect to simulating the conditions in the human GI tract. However, the present invention contemplates the use of the apparatus and method for simulation of other GI tracts where applicable.

In another alternative embodiment (not shown), force application system 300 has a bag or pouch to hold the dosage form 10. Preferably, the bag is made from a wire mesh cloth. The wire mesh cloth is preferably woven and would use an appropriate gauge of wire with a suitable opening size. The bag would abut, or be in proximity to, a piston that is preferably operably connected to the housing 150. The dosage form 10 would be placed in the bag and the bag would be squeezed via the piston so that there would be a gentle force applied to the dosage form 10 by the squeezing motion of the wire mesh bag. This alternative structure and method for applying a force to dosage form 10 via force application system 300 would simulate or mimic the peristaltic contraction of the GI tract.

Figure 6:
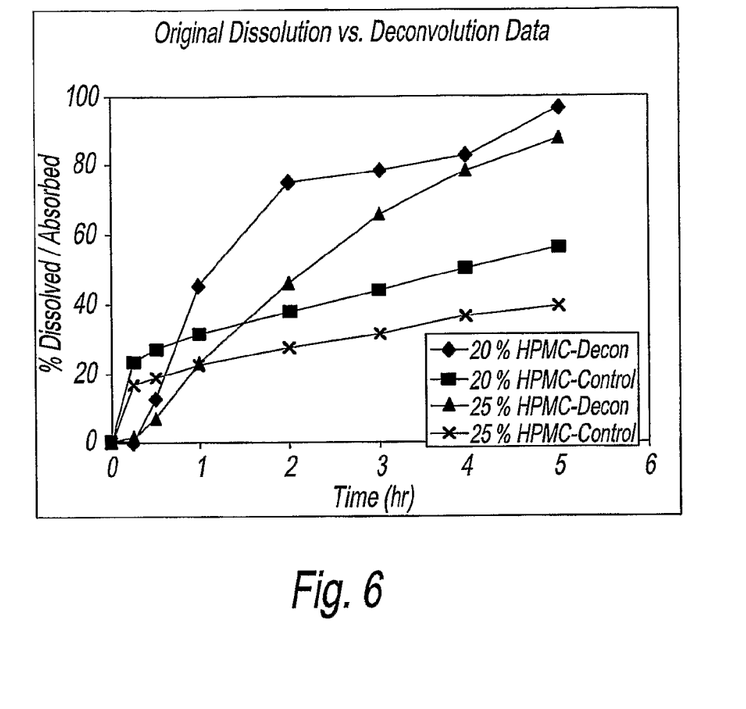
FIG. 6 represents dissolution results for bi-layer matrix tablets over time for a contemporary USP 2 dissolution apparatus ("original dissolution") in comparison to the deconvolution of clinical pharmacokinetics results, where the two formulations vary in the level of rate controlling polymer in the sustained release layer, which in this case was HPMC. The bilayer tablet contains an Immediate Release (IR) layer without HPMC, and a Sustained Release (SR) layer with HPMC.
Figure 7:
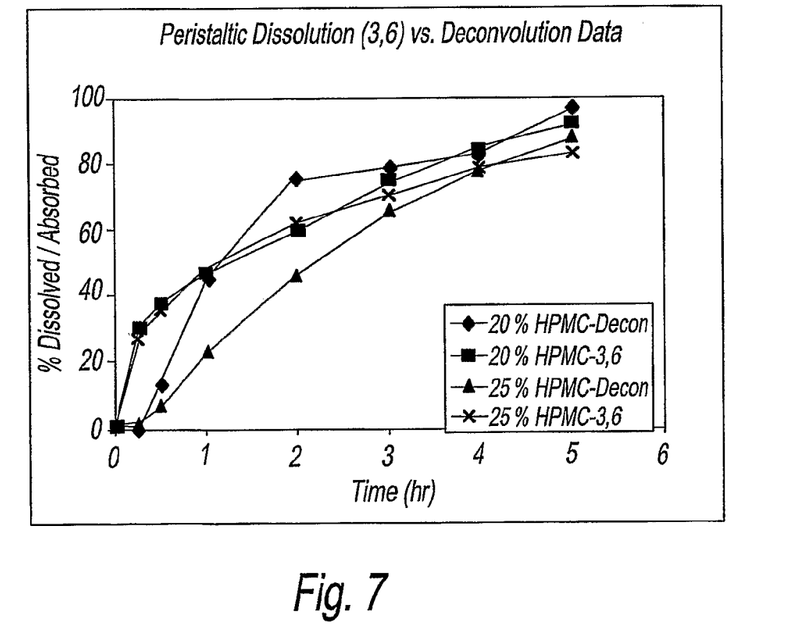
FIG. 7 represents dissolution results over time for the present invention ("peristaltic dissolution") in comparison to the deconvolution of clinical pharmacokinetics results for the bi-layer matrix tablets of FIG. 6.

Referring to FIGS. 6 and 7, a graphical comparison is provided, which is indicative of the improved accuracy of the analysis device 100 as compared to a contemporary paddle-type USP 2 dissolution device for predicting dissolution of bi-layer matrix tablets. The dissolution for the contemporary USP 2 dissolution apparatus ("original dissolution") of FIG. 6 and the dissolution for the device 100 ("peristaltic dissolution") of FIG. 7 are shown in comparison to the deconvolution of clinical pharmacokinetics results for the bi-layer matrix tablet.

For the results shown in FIG. 7, the force application system 300 of device 100 utilized a compression time of three seconds with six seconds in between compressions (i.e., "3,6"). The force was applied using air pressure at 3 bars. The accuracy of device 100 is especially evident over longer periods of time, e.g., release occurring after one hour. The apparatus and method of the present invention provides for more accurate prediction of release and, in particular, sustained release, of the active agent(s). Such accuracy and reliability in predicting release performance may allow for the reduction of the number of clinical studies required of a particular pharmaceutical product, when analyzed by the apparatus and method of the present invention.

Figure 8:
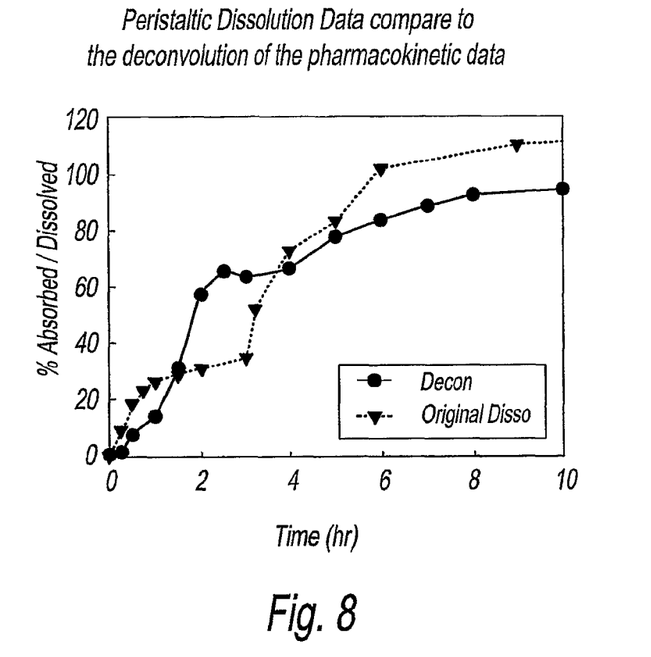
FIG. 8 represents dissolution results for another sustained release dosage form over time for a contemporary USP 2 dissolution apparatus ("original dissolution") in comparison to the deconvolution of clinical pharmacokinetics results.
Figure 9:
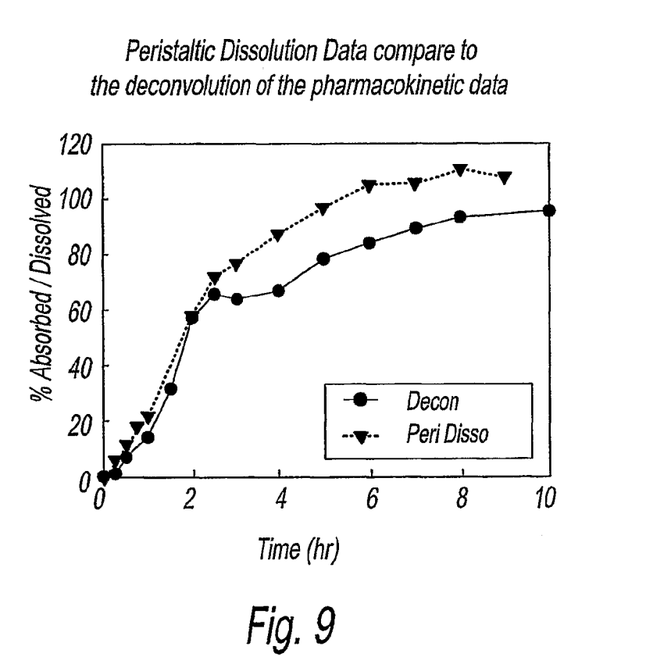
FIG. 9 represents dissolution results over time for the present invention ("peristaltic dissolution") in comparison to the deconvolution of clinical pharmacokinetics results for the dosage form of FIG. 8.

Referring to FIGS. 8 and 9, another graphical comparison is provided, which is again indicative of the improved accuracy of the analysis device 100 as compared to a contemporary paddle-type USP 2 dissolution device for predicting dissolution but of another type of dosage form. The dissolution for the contemporary USP 2 dissolution apparatus ("original dissolution") of FIG. 8 and the dissolution for the device 100 ("peristaltic dissolution") of FIG. 9 are shown in comparison to the deconvolution of clinical pharmacokinetics results for the dosage form.

Device 100 has been described as a single analyzing unit. However, the present invention contemplates the use of a number of devices 100, which can be used for analysis of the dosage form 10. In one such alternative embodiment, there are six devices 100 with each having a force application system 300 that are connected to one another via a common plate, rack or other structure. Such an arrangement allows for simultaneous analysis of a plurality of dosage forms 10 where the force application systems 300 are lowered together into their respective dissolution media (in their respective housings 150) at the beginning of the dissolution run. This alternative embodiment also allows for the use of coordinated control to make the process more efficient.

While the present invention has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments as described herein and in the claims.

What is claimed is:

1. A dissolution device to analyze the release of an active agent from a dosage form in a GI tract, the device comprising:
    a vessel having an open end, said vessel containing a medium; and
    a force application system having a chamber and a force imparting mechanism, said chamber supporting the dosage form and being in fluid communication with said medium, wherein said force imparting mechanism applies compression to the dosage form to simulate conditions in the GI tract.

2. The device of claim 1, wherein said force application system is connected to said open end thereby being positioned in said medium.

3. The device of claim 1, wherein said chamber is a cylinder, said force imparting mechanism comprises a piston, and said piston is operably connected to a power source.

4. The device of claim 3, further comprising a controller operably connected to said piston to control at least one of a frequency, a duration or an amount of said compression that is applied to the dosage form.

5. The device of claim 3, further comprising an impeller that circulates said medium.

6. The device of claim 5, further comprising a sampler that obtains a sample of said medium for analysis.

7. The device of claim 3, wherein said cylinder has one or more slots that allow for flow of said medium into and through said cylinder.

8. The device of claim 7, wherein said cylinder has a mesh screen along a bottom of said cylinder.

9. The device of claim 3, wherein said cylinder has a first mesh screen along a bottom of said cylinder and a second mesh screen above said first mesh screen that sandwiches the dosage form in place.

10. The device of claim 1, wherein said force application system has padding positioned between the dosage form and said force imparting mechanism.

11. The device of claim 10, wherein said padding is silicon.

12. The device of claim 1, wherein said force application system is made at least in part from electropolished stainless steel.

* * * * *